United States Patent [19]
Lemelson

[11] Patent Number: 5,769,787
[45] Date of Patent: Jun. 23, 1998

[54] MEDICAL SCANNING AND TREATMENT SYSTEM AND METHOD

[76] Inventor: Jerome H. Lemelson, Suite 286, Unit 802, 930 Tahoe Blvd., Incline Village, Nev. 89451

[21] Appl. No.: 480,418

[22] Filed: Jun. 7, 1995

Related U.S. Application Data

[63] Continuation of Ser. No. 799,428, Nov. 25, 1991, Pat. No. 5,464,013, which is a continuation-in-part of Ser. No. 717,080, Jun. 18, 1991, Pat. No. 5,456,663, which is a continuation-in-part of Ser. No. 54,277, May 26, 1987, abandoned, which is a continuation-in-part of Ser. No. 614,021, May 25, 1984, Pat. No. 4,671,256, which is a continuation-in-part of Ser. No. 614,038, May 25, 1984, Pat. No. 4,665,897.

[51] Int. Cl.$^6$ .................................................... A61B 5/05
[52] U.S. Cl. ................................................ 600/407; 604/50
[58] Field of Search ....................... 128/653.1, 660.01, 128/660.03, 920; 378/62, 65, 68, 205, 206, 208, 195–197; 364/413.13; 604/50; 601/4; 600/407, 437, 439

[56] References Cited

U.S. PATENT DOCUMENTS

| | | | |
|---|---|---|---|
| 3,349,242 | 10/1967 | Braestrup | 378/65 |
| 3,839,641 | 10/1974 | Cooke et al. | 250/369 |
| 3,971,949 | 7/1976 | Bräther et al. | 378/195 |
| 3,997,793 | 12/1976 | Rogers et al. | 378/205 |
| 4,118,631 | 10/1978 | Froggatt | 378/65 |
| 4,230,129 | 10/1980 | LeVeen | 378/65 |
| 4,365,341 | 12/1982 | Lam | 378/65 |
| 4,481,656 | 11/1984 | Janssen et al. | 378/196 |
| 4,526,168 | 7/1985 | Hassler et al. | 601/4 |
| 4,610,249 | 9/1986 | Makofski et al. | 601/4 |
| 4,649,555 | 3/1987 | Matsubayashi et al. | 378/205 |
| 4,649,560 | 3/1987 | Grady et al. | 378/196 |
| 4,787,371 | 11/1988 | Grasser et al. | 601/4 |
| 4,821,729 | 4/1989 | Makofski et al. | 601/4 |
| 5,044,354 | 9/1991 | Goldhorn et al. | 601/4 |
| 5,537,452 | 7/1996 | Shepherd et al. | 378/65 |

*Primary Examiner*—Brian L. Casler

[57] ABSTRACT

An apparatus, system and method for scanning select tissue of a living being with penetrating radiation and employing such radiation to perform one or more medical functions such as diagnosis and treatment of a disease or malady. In one form a computer is employed to analyze electrical signals generated by one or more transducers sensing penetrating radiation after it has penetrated select tissue of a living being and generates control signals which are employed to control further scanning and/or the operation of a surgical device to cause the latter to perform a select operation on select tissue of said living being. In a particular form, two types of radiation are generated, one to effect inspection scanning of select tissue of a living being and the other to effect a surgical operation on select tissue including the tissue scanned after a computer analyzes the inspection scanning signals generated and generates control signals for effecting the controlled surgical operation. Drug units to be employed in the treatment of select maladies are also disclosed.

13 Claims, 6 Drawing Sheets

MEDICAL SCANNING AND TREATMENT SYSTEM AND METHOD

CROSS REFERENCE TO RELATED APPLICATIONS

This is a continuation of application Ser. No. 07/799,428 filed Nov. 25, 1991 now U.S. Pat. No. 5,464,013 which is a continuation-in-part of application Ser. No. 07/717,080 filed Jun. 18, 1991, now U.S. Pat. No. 5,456,663, which is a continuation-in-part of Ser. No. 54,277 filed May 26, 1987, now abandoned, which is a continuation-in-part of Ser. No. 614,021 filed May 25, 1984, now U.S. Pat. No. 4,671,256, which is a continuation-in-part of Ser. No. 614,038 filed May 25, 1984 now U.S. Pat. No. 4,665,897.

SUMMARY OF THE INVENTION

This invention relates to an apparatus and method for scanning the body of a living being with penetrating radiation which, in a preferred form, is generated as a beam or beams directed through a select portion or portions of the body wherein information signals relating to select tissue scanned is analyzed by a computer which is employed to control further scanning and/or the operation of apparatus, such as a surgical device, for correcting or eliminating a malady by controllably operating on select tissue such as a tumor, scar tissue or other tissue requiring select treatment with radiation or a mechanical device. The radiation treatment may vary from controllably heating select tissue to effect, promote or accelerate a curing action and, in certain treatment procedures, to enhance the action of a drug applied locally to the tissue irradiated to a surgical action in which select local tissue at or near the surface of the skin or deep within the body is selectively destroyed.

Accordingly it is a primary object of this invention to provide a new and improved apparatus and method for performing a medical procedure under the control of a computer.

Another object is to provide a computer controlled radiation scanning system and method for treating maladies in living beings.

Another object is to provide an apparatus and method for scanning select tissue of a living being with radiation to detect maladies such as tumors and computer controlling a surgical means to operate on a select portion of the tissue scanned.

Another object is to provide an apparatus and method for detecting the presence and location of a malady, such as a tumor in the body of a living being with radiation and automatically operating on such malady with auxilliary radiation.

Another object is to provide an apparatus and method for automatically operating on select tissue of a living being with a surgical tool to the exclusion of normal or healthy tissue.

Another object is to provide a system and method for automatically detecting the presence, extent and location of a tumor such as a cancerous growth within the body of a living being and generating information and control signals in accordance with the extent and location of such tumor.

With the above and such other objects in view as may hereinafter more fully appear, the invention consists of the novel apparatus and methods for scanning, detectin and treating tissue maladies as will be more fully described herein, but it is to be understood that changes, variations and modifications may be resorted to which fall within the scope of the invention as claimed without departing from the nature and spirt of the invention.

Accordingly it is a primary object of this invention to provide new and improved methods for treating diseases and deficiencies in living beings and drug units employed in such methods.

Another object is to provide a method for treating cancer in the body of a living being.

Another object is to provide a method for treating cancer in the blood of a living being.

Another object is to provide a method for treating leukemia in a living being employing drug units which are targeted to imature leukemic or white blood cells in a precancerous state by releasing a drug or drugs directly against the outer surfaces of such cells and causing same to penetrate and beneficially affect or restore the regulatory apparatus of the cells to cause such cells to mature normally.

Another object is to provide drug units and methods for treating various diseases such as various types of cancer in the bodies of living beings by targeting select small quantities of select drugs to select tissue and/or blood cells of a living being.

Another object is to provide drug units and methods for preventing the spread of cancer through the body of a living being having cancer by targeting small quantities of select cell killing and/or cell regulating chemical and/or biological drugs to select cancer cells in the blood of a living being select portion of which quantities are caused to penetrate the cell walls, enter and kill or render the cells noncancerous or incapable of abnormal division and causing the spread of cancer.

Another object is to provide improved methods for preventing a disease or its proliferation in the body of a living being by detecting with one or more detection means of an implant the presence of select disease cells in a body fluid such as the blood of a living being, computer processing and analyzing detection signals generated by such detection means and generating control signals for controlling the release of a select quantity or quantities of a disease controlling or killing drug to the body from a reservoir or reservoirs in the implant.

Another object is to provide drug units which are operable to carry small quantities of a select drug which is carried by the drug unit to and adjacent select diseased or disease spreading cells and is operable to become bound to a targeted disease cell and to release such drug against the cell, whereby the drug penetrates and floods the cell to kill the cell without destroying the cell wall to permit the cell and the drug it contains to be removed from the body without causing damage to normal cells of the body.

Another object is to provide drug units which are operable to carry small quantities of a select drug which is contained in the drug units to select cells in the body and to release and deliver a quantity of such drug to the surfaces of the select cells wherein the drug enters the cells and is operable to beneficially affect the cell control mechanism by restoring same to normal operation and/or preventing the abnormal operation thereof.

Another object is to provide drug units and methods for delivering a drug or drugs contained therein directly to select tissue or blood cells in a manner to cure a disease such as as cancer by destroying the cells thereof and/or rendering same benign.

Another object is to provide and apparatus and method for detecting and treating cancer with a drug or drugs targeted to select cancer cells of a tumor in a living being.

Another object is to provide improved methods for delivering disease fighting or killing drugs directly to disease sites such as infected organs or tumors by means of drug units targeted to such sites or select cells, so as to reduce harmful side effects of such drugs to normal cells and tissue.

Another object is to provide a method for treating a plurality of diseases simultaneously in a living being.

Another object is to provide new drug units useful in the simultaneous treatment of a number of diseases in a living being.

Another object is to provide a method for treating a disease caused by the proliferation of disease causing virus within select cells of a living being by destroying such virus within host cells before they multiply and destroy the cell and escape therefrom.

Another object is to provide drug units and a method for arresting or curing acquired immune deficiency syndrome disease in living beings and drug units employed in such method.

Another object is to provide drug units and methods for simultaneously treating a plurality of diseases including AIDS and one or more infectious diseases resulting therefrom wherein a plurality of drugs are targeted to selected AIDS infected cells of the body and to select infectious material and/or cells at sites containing such infectious material to simultaneously destroy the AIDS virus and/or cells containing same and virus, fungus, bacteria or combinations thereof defining one or more diseases other than AIDS.

Another object is to provide drug units and methods destroying or regulating and supressing select diseases wherein radioactive tracer means is employed in or along with the drug units and is targeted therewith to select cells and disease sites and are employed as a means for detecting the density of the drug units targeted to a select disease site or organ to indicate and/or provide information for controlling treatment means such as drug delivery means.

With the above and such other objects in view as may hereinafter more fully appear, the invention consists of the novel compositions of matter and methods for utilizing same in treating and controlling disease in a living being, but it is to be understood that changes, variations and modifications may be resorted to which fall within the scope of the invention as claimed.

DESCRIPTION OF THE DRAWINGS

In the drawings:

In FIG. 1 is shown broad details of the components and subsystems of a computerized scanning and control system for the radiation treatment of living matter, such as a living human being such as in the treatment of various diseases.

Figure 1:
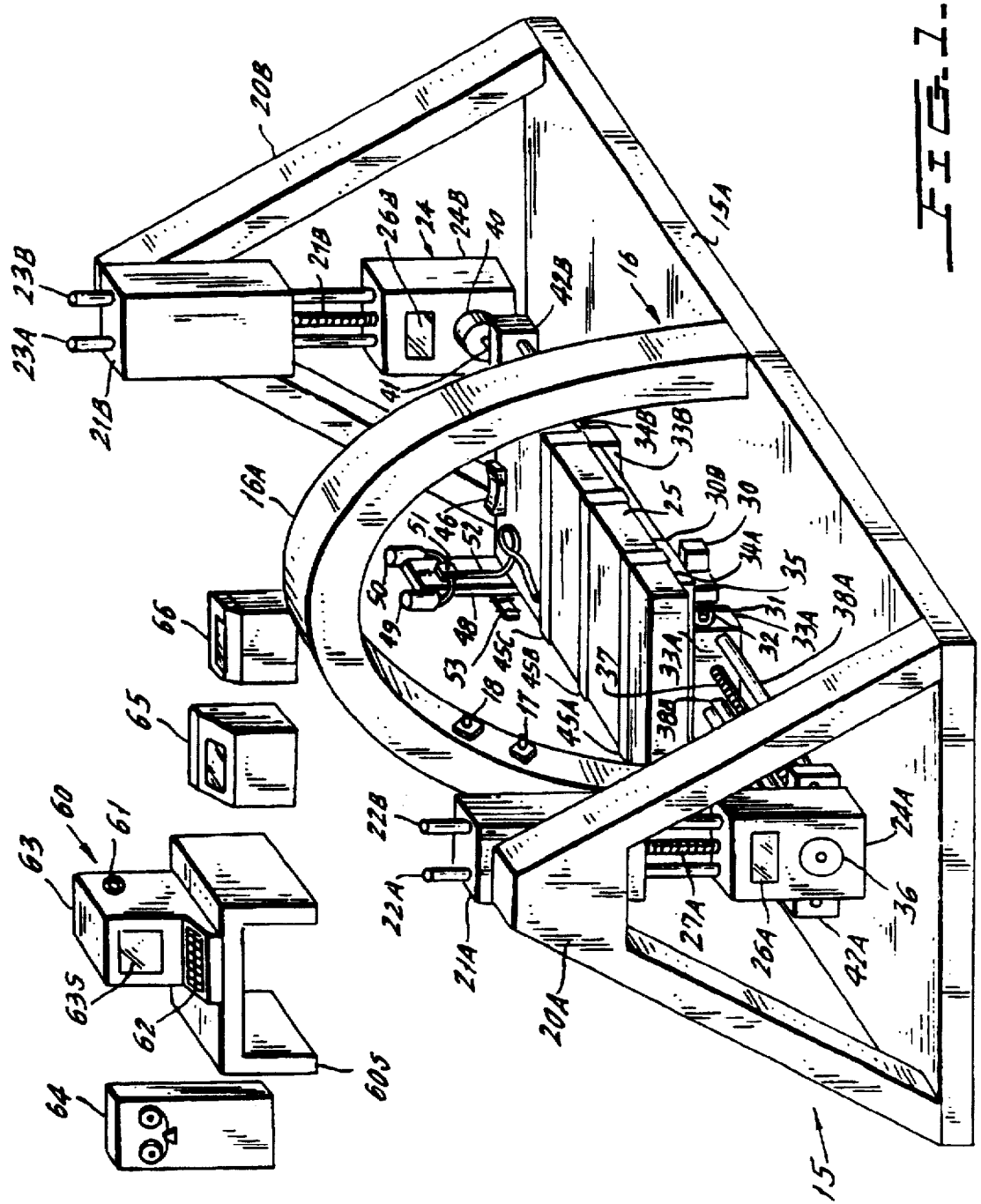
FIG. 1 is an isometric view of components and subsystems of a medical detection, monitoring, disgnosing and treatment system for human beings including patient scanning and monitoring apparatus, a computer for controlling such scanning apparatus, a video display, a character printer and a graphics printer.

A first assembly 15 includes a platform, mount or base 15A which supports an upstanding arcuately shaped frame or rail 16 defining a rigid support and housing 16A containing a plurality of sensor-emitters, namely radiation-detectors 17 and radiation emitters 18. Such frame or rail 16 is constructed and is shown as supporting one or more transducing assemblies, each containing one or more radiation detectors 17 and radiation emitters 18 which will be described in greater detail. Also supported by platform 15 is a support table or couch 25 and end frames or supports in the shapes of A-frames 20A and 20B. Supported by the end A-frames 20A and 20B are respective couch support blocks 21A and 21B, each containing respective pairs of vertically aligned slide bearings for slidably supporting respective pairs of vertically extending cylindrical shafts denoted 22A, 22B and 23A, 23B, each of which pair of shafts support respective solid end blocks denoted 24A and 24B at their ends, between which blocks extend a pair of parallel shafts 38A, 38B supporting the couch 25. The assembly of the couch 25, shafts 38, end blocks 24 and vertical shafts 22 and 23, is thus supported for z-axis vertical guided movement by blocks 21A and 21B. Z-axis powered adjustment of the vertical position of the couch 25 is effected by the controlled operation of a pair of motors 26A and 26B, which may be signal controllable reversible gear-motors or stepping motors which are respectively supported by the blocks 24A and 24B. Said motors rotate lead screws 27A and 27B causing such lead screws to advance or retract the shafts in threaded holes centrally disposed in respective support blocks 21A and 21B.

X-axis controlled positioning of the table or couch 25 is effected by the controlled operation of a reversible stepping or feedback signal controlled gear-motor 30 which is supported by a block 30B which supports and guides table 25 in movement laterally across and above lower platform 15A. Motor 30 is coupled to rotate its lead screw 31 about an X-axis causing such screw to advance or retract through a threaded bearing 32 in a base support block 33A. A base support 34A for the couch 25 is attached to a support plate 35 for motor 30. Base support 34A is also attached to block 33A by sliding guides (not shown) permitting smooth X-axis motion thereof. A similar base support 34B is also shown in part and such support is attached to support block 33B by similar X-axis sliding guides to permit suitable X-axis adjustment of the position of the couch or table 25.

Y-axis motion of the couch 25 is effected by the controlled operation of a reversible stepping or feedback signal controlled gear-motor 36 which is supported by a block 24A, which motor rotates a Y-axis lead screw 37 causing said screw to advance or reverse travel with respect to the bearing guide defined by a threaded bore in blocks 33A & 33B for effecting Y-axis movement of the couch. Smooth linear Y-axis adjustment is ensured by supporting blocks 33A and 33B on sliding guiderails 38A and 38B.

Controlled rotation of table 25 is effected by the controlled actuation of a geared stepping motor or a rotational position feedback controlled motor 40 supported by block 24B. Controlled operation of a gear motor 40 effects the controlled rotation of a shaft 41, which in turn causes end supports 42A,42B affixed to the rails 38A and 38B to rotate, causing the entire couch assembly supported by such rails to rotate about a horizontal axis. Also provided attached to the couch 25 are a plurality of patient restraint straps 45A, 45B and 45C and a headrest 46. Such straps and headrest are employed to maintain the patient in a fixed position on the couch 25 as the couch moves during a monitoring and/or treatment cycle. The upper face of the couch 25 may also be provided with lines or grid marks and numerical indicia for use in properly positioning and repositioning a patient thereon and in analyzing the results of scanning and treating such patient in the manner which will be described hereafter.

Also illustrated in FIG. 1 is an intravenous drug dispensor stand 48 which is supported above the base 15 by suitable means. Supported by stand 48 are a plurality of reservoirs, such as removable bottles 49 and 50 for containing a plurality of different drugs to be administered to the patient during monitoring or disease detection and/or during the treatment thereof in the manner to be described. The administration of such drugs may be effected in an automatic manner by means of respective solenoid control valves or motors which are automatically controlled to operate pumps or valves in a manner to regulate and control the flow rate of liquids from such reservoirs. Notation 51 refers to a control switch and 52 to an intravenous injection flow tube which will be described. Also supported by stand 48 is an intravenous needle rack 53 for the storage of such auxiliary needles and intravenous injection accessories as are necessary to properly effect the monitoring and treatment of disease of a patient disposed on the couch 25.

Also shown in FIG. 1 are units including housings containing electronic controls and interface equipment for the proper operation of the computerized scanning and control system. A stand 60S supports a housing 60 containing an assembly 60A which contains a computer and an electronic control system 10 for controlling the operation of the computerized scanning and control system. Such stand also supports a speaker 61, a user accessible keyboard 62 and a video display 63 having a monitor screen 63S which may be used to display command and control information, to display monitorable data including digital data and graphical or reconstructed image data to permit the real time observation of internal tissue and organs of a patient as well as data generated in the past so as to permit the review of previously recorded data derived from scanning signals output by sensors employed and image information derived therefrom. A mass storage device 64, is provided which may comprise an erasable magnetic disc or tape recorder-reproducing unit, such as a floppy or hard disc storage system or other form of rapid access archival mass storage means. Additional peripheral equipment includes a line printer 65 and a graphics plotter 66 which may be used to provide respective forms of hard copy defined by signals output by the computer or computers employed in the system and by signals generated by the detectors employed. While the computerized scanning and control system for radiation treatment is shown as an assembly of separate functional components or modules, an integrated construction may be employed in which all of such described equipment is supported by the base 15, preferably in a single housing or group of housings which are adjacent each other.

Figure 2:
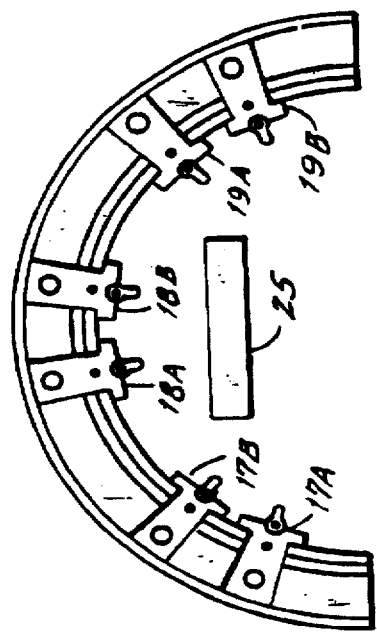
FIG. 2 is an end view with parts removed for clarity of an arcuately shaped mount for a plurality of radiation beam emitters and sensos forming part of the apparatus of FIG. 1.

In FIG. 2 is shown details of the internal construction of the support 16 for a plurality of radiation sensors and, if employed, emitters mounted on the arcuate support 16. A plurality of radiation detectors 17A and 17B and a plurality of neutron beam sources 18A and 18B and X-ray emitters 19A and 19B form part of the system. All detectors/emitters are supported below the upper portion of arcuate track 16B which defines the main support for frame 16. Each detector-emitter contains a reversible gear motor and may thus be driven to any position on the gantry 16 by utilizing a toothed track 70 which is affixed to the arcuate track or gantry 16.

While but two adjacently located sensor/emitters of each type are illustrated and are used within the current embodiment, the system may comprise an additional number of such sensor/emitters capable of being positioned or driven to any select locations along the track of the gantry 16. A larger number of sensor/emitters will allow faster and, in certain instances, more highly resolved operation of the system and may be utilized where such higher resolution and faster operation are requisite or desired.

Figure 3:
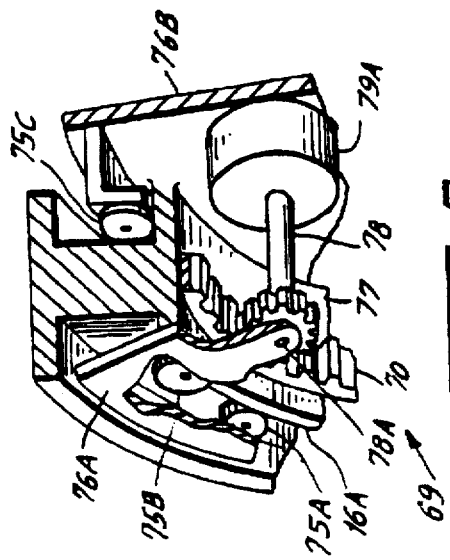
FIG. 3 is a partical isometric view with parts sectioned and broken away for clarity of a mounting arrangement for the positionable sensors and/or emitters of FIG. 2.

In FIG. 3 is shown a typical mounting arrangement 69 for a typical sensor/emitter pair on the gantry track 16. A plurality of pairs of wheels 75A/75B supported on respective sensor support face plates 76A and 76B permit rolling movement along the inner surface 16S of the I-cross section shaped gantry track 16. Tension is maintained between such wheels and the inner surface 16A by a drive gear 77 supported by the face plate 76 on a shaft 78 extending through a bearing 78A and a gantry supported track gear 70. Circumferential positioning of the sensor support assembly on the gantry 16 is accomplished by the actuation of a geared stepping motor or a shaft position/rotation encoded motor 79 which is supported on face plate 76B.

Figure 4:
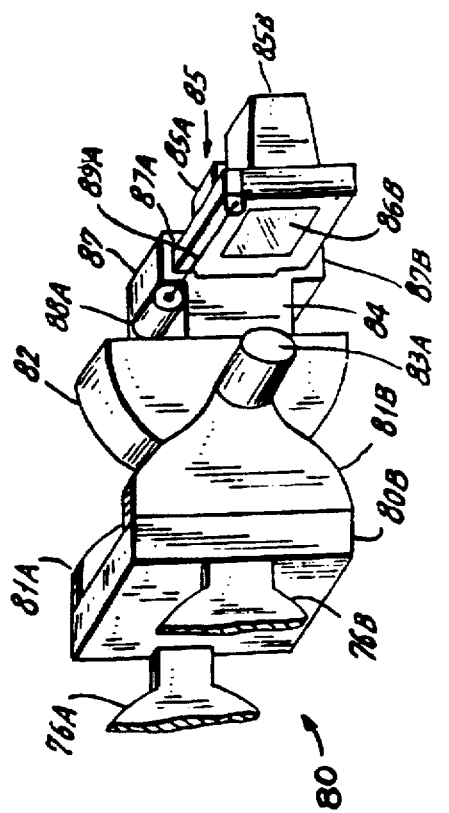
FIG. 4 is an isometric view with parts broken away for clarity of the support assembly for the sensors and/or emitters of FIG. 2.

FIG. 4 illustrates further details of the construction of an emitter/detector support assembly 80. Attached to and supported by face plates 76A and 76B is a base 80B for rotationally supporting the sensor assembly, from which base extends a pair of pivotted supports 81A and 81B. A sensor base counter-weight 82 is shown supported by a rotatable axle which passes through the center of gravity of counterweight 82 and is driven in rotation by a reversible feedback controlled or stepping motor 83. Such rotation effects controlled angular positioning of the affixed sensors within the plane of the gantry track 16.

The radiation scanner may comprise a scintillation counter and/or a television camera or the like. In the form illustrated, a light proof housing 84 contains a photomultiplier tube or its equivalent and associated optics as in FIG. 5. In FIG. 4, the radiation to be detected travels from right to left and enters a radiation collimator 85 and passes therethrough to a suitable scintillation or phosphorescent screen 86A. The secondary light emission from such screen is detected by the photomultiplier. A single photomultiplier and positioning assembly may be employed to detect either or both X-ray and gamma radiation by means of appropriate collimator design and material and the use of a secondary emission screen. A single assembly is shown constructed with a gamma ray collimator 85B and scintillation screen 86B affixed parallel to an X-ray collimator 85A and secondary emission detection screen 86A which assembly may be shifted laterally with respect to tracks 87A and 87B of a guide 87 to position the collimator/screen assembly along the optical axis of the photomultiplier. Such lateral assembly shift is accomplished through a force transmission rod 89A by the actuation of a solenoid or motor 88A.

Figure 5:
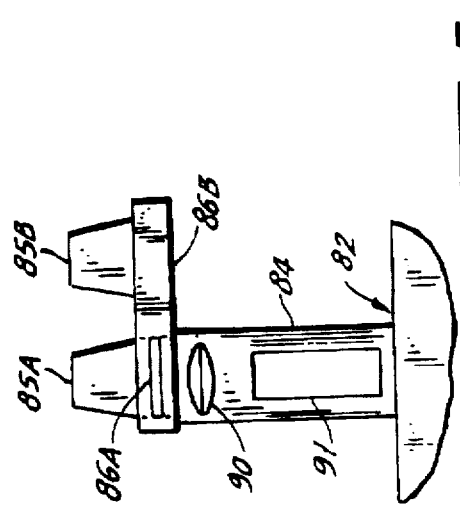
FIG. 5 is an end view showing details of a typical sensor assembly of the type shown in FIG. 2.

FIG. 5 shows details of the detector assembly. A focusing lens 90 collects the light from the detector screen 86A and focuses it on the photocathode of a photomultiplier tube 91 for detection.

Figure 6:
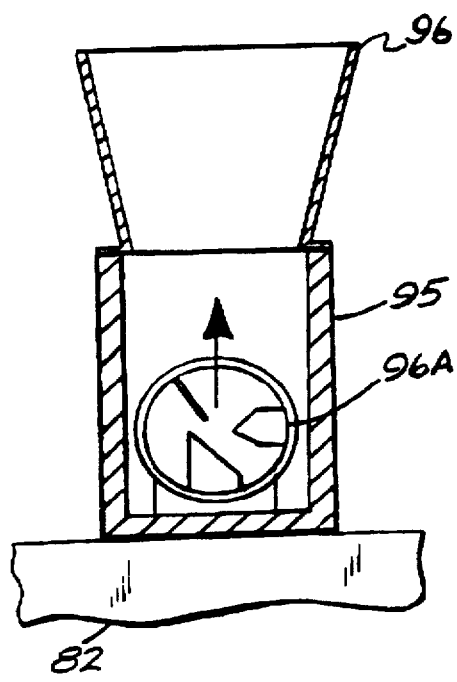
FIG. 6 is an end view with parts broken away for clarity of an X-ray emission means and assembly therefore applicable to the apparatus shown in FIGS. 1 and 2.

FIG. 6 shows details of the construction of an X-ray projection source which may be employed, as described, in the computerized scanning and control system. A radiation shielding cannister 95 contains an X-ray tube 96A. Also supported by the cannister 95 is an X-ray modulator and dispenser 96, which produces a fan-shaped exit bean of uniform intensity and known angular divergence in a two dimensional plane.

Figure 7:
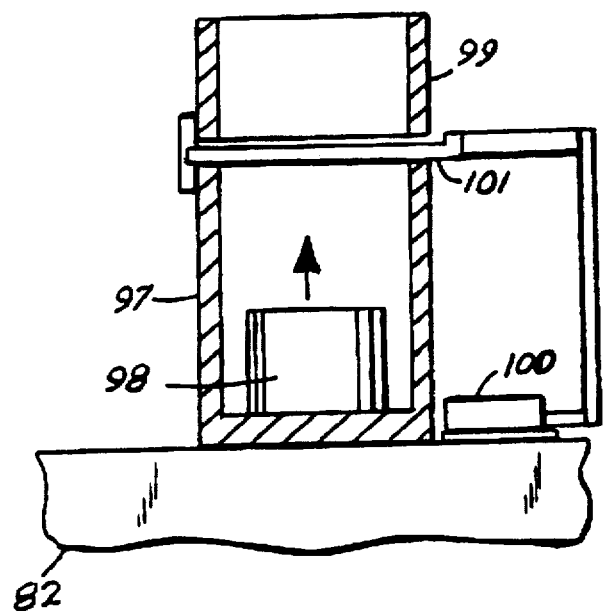
FIG. 7 is an end view with parts sectioned for clarity of a source of neutron beam radiation and its mechanical gating means applicable as an radiation emitter for use with the apparatus of FIGS. 1 and 2.

In FIG. 7 is shown a construction similar to FIG. 6 wherein a source of neutrons replaces the X-ray source. Enclosed in an open ended housing 97 is a neutron-neutron source material 98. Supported by housing 97 is a neutron collimator 99 which only allows well collimated neutrons to exit therefrom along a pointing or directed axis. Neutron flow intensity is controlled by the actuation of a solenoid 100 which slides a shutter 101 constructed to block neutrons from the source, into and out of the path of the neutrons.

Figure 8:
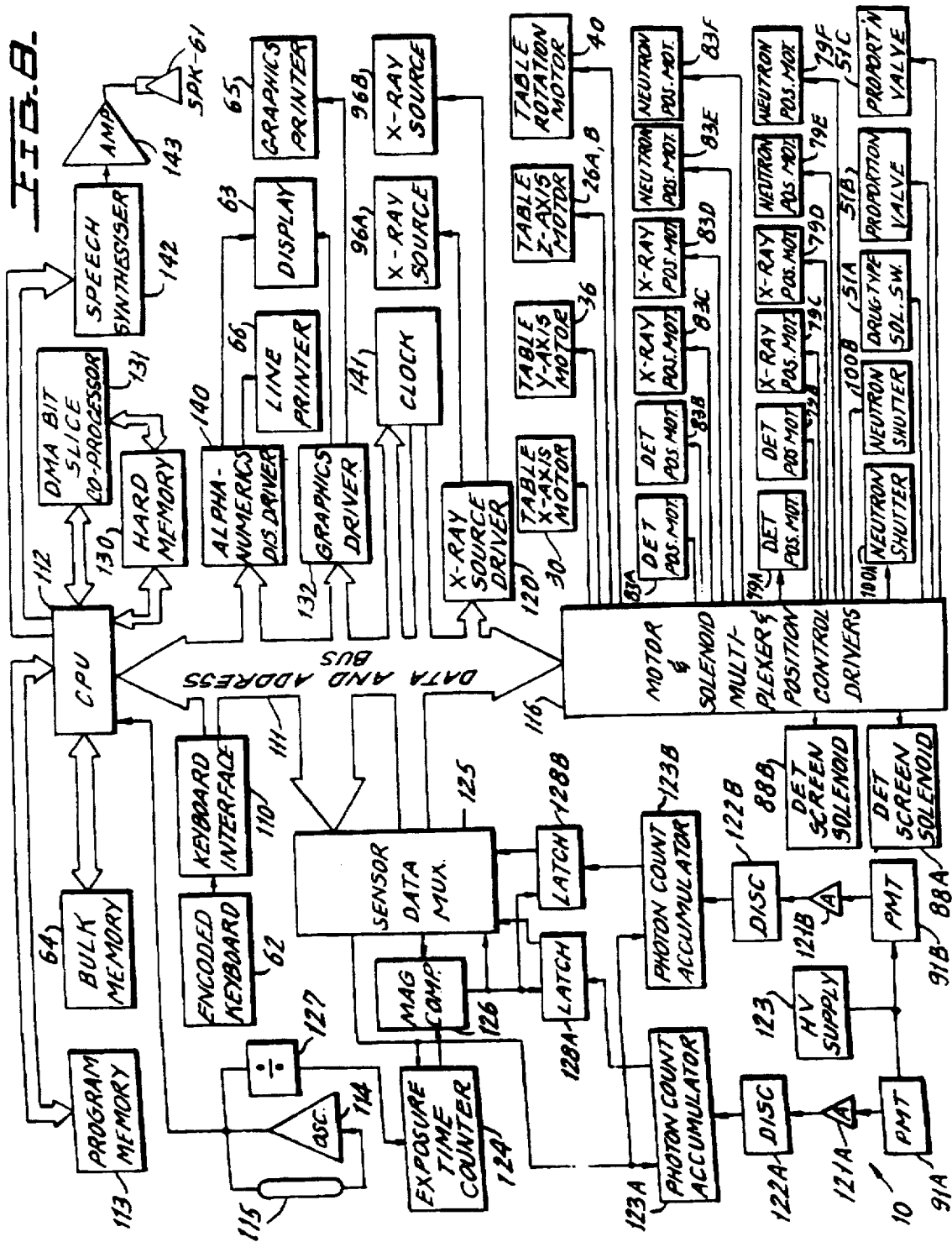
FIG. 8 is a schematic diagram illustrating an electronic control system and subsystem components of the medical monitoring, scanning and treatment system illustrated broadly in FIG. 1.

FIG. 8 shows details of the electronic control system for the computerized scanning and control system for radiation treatment. Such system 10 may be manually addressed or controlled by an operator who enters system commands as are necessary by the selective operation of the keys of keyboard 62. Such input instructions are transferred via a keyboard interface 110 and a system bus 111 to a central processing unit 112 of a digital computer wherein they are electronically processed according to the instructions recorded in a program memory 113. Central processing unit timing and synchronization are accomplished by means of a frequency stable oscillator 114, having suitable feedback means such as a crystal 115, the output signals of which oscillator are employed for such synchronization.

Cycle starting may commence after a patient is positioned on the couch or table 25 on which such patient is predeterminately located and retained by strapping so that the body or portion of the patient desired to be monitored and treated, is within the plane of the sensor mounted gantry housing 16. Positioning information is derived from signals entered by the selective operation of the keys of the keyboard 62 or is reproduced from previously recorded coordinate signals provided in mass memory 64. Parameters relating to the desired positioning of the patient couch or table 25 at a selected X, Y and Z coordinate location with respect to the base and a selected tilt or rotational position with respect to its longitudinal axis is effected by means of signals generated from the central processing unit 112 and transmitted on bus 111 through multiplexers 116 for the respective motors and solenoids, wherein the position command codes derived are interpreted as proportional electrical signals which are applied to control the X-axis motor 30, the Y-axis motor 36 and the Z-axis motors 26A and 26B as well as the table rotating motor 40. The motor multiplexer and driver 116 are not detailed as such devices are well known in the art and generally contain address and data decoders and device drivers or stepping motors for effecting the desired movements.

Once the patient has been predeterminately positioned, the functional operation of the system in monitoring and/or radiation treating the patient may be initiated. A computer axial tomography scan may be initiated by computer or manually controlled positioning of the X-ray sources 96A and 96B by means of signal control of the X-ray source position motors 79C and 79D and the tilt position motors 83C and 83D resulting from signals generated by the central processing unit 112 and transmitted on bus 111 to the motor multiplexer and control drivers 116. Signals transferred from the central processing unit (CPU) 112 on bus 111 also comprise data which is employed to control the operation of motors 79A, 79B and 83A, 83B which respectively position the photomultipliers 91A and 91B along the track of the gantry and effect predetermined tilting or rotation of the photomultipliers on their mounts to properly aim same to detect radiation generated within or passed through the patient. When all select or predetermined patient source and detector positioning commands have been generated and applied and, when the X-ray sensitive detector screens 85A and 85B have been selected by the proper actuation of screen solenoids 88A and 88B in response to instructions received from the CPU 112 which are transferred via bus 111 and the solenoid multiplexer and driver 116 are activated, a computerized axial tomography (CAT) scan may begin.

The X-ray sources 96A and 96B are generated at intensities defined by data incorporated in signals received from the CPU 112, which signals are transferred via bus 112 to X-ray source driver 120. X-ray source patterns are predeterminately selected so as to be appropriate for effecting fan projection tomography (FPT).

The X-radiation detectors are operated in a photon counting mode as follows: X-rays which are transmitted through the patient's body are attenuated differently along different rays of the fan projection according to variations in the internal structure density of the patient. Since each of the optic axes of the photomultipliers 91A and 913 point along different rays emerging from sources 96A and/or 96B which have been attenuated by the patient's body, the phosphorescent screen in front of each detector (91A and 91B) will emit radiation and glow according to the intensity of the transmitted X-rays and such light creates proportional photon pulse signals from the anodes of each detector when an appropriate high voltage supply 123 is connected to the dynode chain of each photomultiplier tube. Such pulse signals are amplified in amplifiers 121A and 121B and are conditioned by pulse discriminators 122A and 122B. The pulse output of each discriminator 122A and 122B is counted and accumulated in the photon counters 123A and 123B. At the time the X-ray intensity measurement starts, the CPU generates and sends a reset signal to the exposure time counter 124 via bus 111 and sensor data multiplexer 125 while simultaneously loading a count number which is proportional to the desired exposure time into a magnitude comparator 126. When the count of clock pulses generated by oscillator 114 and passed through a divider 127 to a counter 124 attains the preset count applied to the input of the magnitude comparator 126, the output of comparator 126 receives a true value which sets a plurality of photon data count latches 128A and 128B to the current photon count intensities set in such counters. The signal output by the comparator 126 also causes a bus interruption to the CPU 112 which allows the CPU to reset counter 124 and the photon counters 128A and 128B through bus 111 and multiplexer 125 and also transfers the count outputs of latches 128A and 128B to a memory 130 (via MUX 125 and bus 111) for further processing.

A full computerized axial tomography scan function may consist of many intensity readings derived when the detectors are positioned at slightly different locations as previously described, for each CAT scan but with the optic axis of the detector unchanged and located along a ray axis of the source. Two detectors are shown, in order to simplify the drawings, but additional detectors may be provided to permit additional rays to be sampled for each scan or shot, thus decreasing the scan time and the total patient X-ray dose. If such additional detectors are employed, they preferably are located to use equiangular spacings to facilitate their implementation in the described fan-projection mode. Analysis and reconstruction of the tomographic image may also be accomplished in real time, independent of the concurrent operation of the CPU 112, from the signals derived from X-ray sampling by means of a fast co-processor 131, such as a bit slice processor, having hardware multiplication implementation, which also has direct memory access capabilities. Once image reconstruction has been accomplished, such as by implementation of the Fourier slice theorem algorithms which are well known in the art, the reconstructed image may be placed at a select location in a memory 130 for later access and use by the CPU 112.

Immediate display of the computer reconstructed image may be accomplished by instructing the central processing unit 112 to transfer the image data recorded in memory 130 to a graphics driver 132 wherein representative analog video signals are generated which are conducted therefrom to display monitor 63. Alternatively, graphics driver 132 may be operable to convert and transfer such image information to a graphics or film printer 65 to provide hard copy of such image information.

The image information stored in memory 130 may be used for the detection and location of a malignant or nonmalignant tumor or otherwise diseased internal body organ or bone. The system may thus be further used both for the detection and analysis and treatment of tumors and the like. In such a detection mode, the coordinates and density of the tumor and the surrounding body tissue may be calculated based on the results of analyzing the image information derived from one or more computerized axial tomography scans or scanning sweeps. Such derived information, including information for assisting or guiding an operator of the equipment, if so operated, may be used to administer suitable chemical or radiation generating drugs to the body of the patient from such reservoirs under the control of respective proportioning valves 51B, 51C, etc. controlled by signals generated by CPU 112 in accordance with computer processing the image information and instructions received from program memory 113, as well as comparisons with past data stored in memory 64. Such control or actuation signals are passed from the CPU 112 via bus 111 and MUX and driver 116 to the drug delivery controls 51A, 51B and 51C for effecting control of the delivery of the one or more drugs controlled thereby.

Further CAT scans may be taken concurrently with the administration of the drug or drug units described or at one or more calculated or predetermined times after such drug or drug units are administered. For the delayed administration of the drug or drugs, the system positioning parameters and image data are transferred to the bulk memory 64 via CPU 112 for later reference.

An alternative automatic control means is provided for adaptive radiation therapy. Such mode of operation is similar to the mode defining the step set forth above. The drugs administered in this mode are either radionuclides which generate a low level of detectable radiation or nuclides, such as boron 10, which become radioactive when receiving and absorbing radiation such as neutrons. The drug units containing such nuclide or nuclides travel through the body via the bloodstream. After the elapse of sufficient time for the drug units to be targeted by means of their antibodies to dispose the nuclide or nuclides adjacent specific antigens, such as existing at or within one or more tumors or abnormal growths or in infected tissue, system 10 may be automatically operated to predeterminately steer and position one or more collimated neutron sources using the tumor position information derived from the described CAT scan, or a CAT scan employing detectors or radiation generated by the nuclide units when activated with externally generated neutron radiation or the like. Such detector and emitter positioning is accomplished by means of command control position signals generated by the CPU 112 which are applied to driver 116 to the neutron source positioning motors 79E and 79F and the neutron source tilt motors 83E and 83F. Once so predeterminately positioned, exposure of the cells of the tumor to the destructive effects of radiation or particles generated by the neutron activated nuclide particles of the combined drug units at the tumor site is effected in a controlled manner by signals reproduced from the CPU 112, which signals control actuation of the respective neutron source shutter solenoids 100A and 100B. Progress attained in effecting tumor destruction and information related to the in situ radiation generated, may be monitored as follows. The radiation detectors are switched to their gamma-ray sensitive operating mode by signals generated by the CPU 112 by the actuation of a pair of detector screen solenoids 88A and 88B via bus 111 and MUX solenoid driver 116. An emission tomography scan may then be accomplished in the same manner employed in effecting the previous CAT scan but without the use of the X-ray source, since the activated nuclides, which are carried by the drug units adjacent the tumor site and/or within the tumor, provide sufficient radiation to effect imageing per se or tumor destroying radiation containing suitable image radiation. The results of the neutron bombardment of the tumor site and the units of nuclide thereat may thus be monitored continuously by effecting the adaptive control of the positioning of the source of neutron, their intensity and direction through the body along a select path or paths or controlled scanning path movement with respect to the tumor site so as to predeterminately provide radiation for monitoring and treating or destroying cells of the tumor in accordance with the information derived from such monitoring and the controlled administration of the nuclide containing units to the body as described.

A further modification of such method allows the system to operate in a manner similar to that previously employed in effecting adaptive radiation therapy in which the nuclide does not itself become radioactive but undergoes a local chemical change under the influence of an applied neutron flux. In this mode of operation, CAT scans may be effected by repeated X-ray projection tomography in order to monitor and check on the progress of the therapy. Otherwise operation of the system may be identical to that which is previously described.

Additional functions of the system, as indicated in FIG. 8, may comprise the display of alpha-numeric command-control and data information on the monitor 63 in accordance with signals transmitted thereto from the CPU 112 to an alpha-numeric display driver 140 which converts such signals to video signals for properly controlling the display writing means. Alternatively, such command control signals and data signals may be appropriately converted and transferred from the driver 140 to the line printer 63 for producing hard copy thereof.

A system clock 141 is included to permit data and time information to be automatically recorded along with other pertinent patient data, CAT scans and treatment progress by the printer 63 or to be displayed on the display screen.

To further facilitate the operation of the system, a speech synthesizer 142 is provided which is addressable by the CPU 112 to allow the system to present sounds of words defining patient data, effect warning conditions or other communications with respect to the operator of the system. Speech synthesizer 142 provides electrical output signals which are amplified in an amplifier 143 and converted to analog speech signals by a loud speaker 61.

It is assumed that suitable power supply means is provided on the correct sides of all electronic components and subsystems of the apparatus described herein to properly perform the computing and control functions described.

Further modifications to the invention described are noted as follows:

1. The drug units described which are employed to carry and apply nuclide material to selected sites in the body, such as cancerous tumors and the like, may be made with recombinant monoclonal antibodies which are synthetically produced by genetic engineering from natural antibodies, which contain a receptacle for receiving and holding matter bound thereto. One or more particles of one or more of the described nuclides may be contained by such recombinant monoclonal antibody receptical to better retain the inactive nuclide in assembly with the antibody and permit a greater amount of nuclide to be so retained and form part of the drug unit for delivery thereby to the tumor together with the nuclide materials bound to the recombinant monoclonal antibodies of the other drug units administered to the patient as part of a single or plural doses thereof.

2. In addition to containing normally inactive nuclide material or particles against or within the confines of the receptacle of the recombinant monoclonal antibody, a small quantity of a tumor killing agent may also be combined therewith and retained by or in the receptacle of the recombinant monoclonal antibody to be released therefrom prior to, during and/or after the nuclide material is activated by neutron radiation at the tumor site as described to provide a combined radiation and chemical attack on the cancer cells of the tumor. If a cell destroying agent, such as a chemical or biological agent is so combined with a recombinant monoclonal antibody and a nuclide capable of being activated as described with neutron radiation beamed through the body to the site containing an accumulation of such drug units, activation of the nuclide may be utilized to effect the controlled release of the cancer killing or modifying chemical or biological agent from the targeted drug units. In one form, such activation is employed primarily to release the cancer killing agent to permit it to destroy cancer cells. In another form, the combined effects of the radiation released when the nuclide material of the drug units is activated with neutron radiation beamed through the cancer site from the exterior of the body and the chemical released from encapsulation in the drug units by the effects of the nuclide radiation, as described, may be employed to destroy the cancerous growth.

3. In addition to the use of neutron radiation in the form of a precisely directed and controlled bean of neutrons operable to activate nuclide material at a cancer or tumor site, auxilliary radiation may also be applied in the treatment and destruction of cancer, either simultaneously with the neutron beam or sequentionally before and/or after the application of the neutron beam. Such auxilliary radiation applied to assist in or effect the destruction of cancer cells, may be in the form of one or more streams of neutrons per se passed through the body of the patient to the cancer site and controllably generated for a select duration or durations of time, to selectively destroy cancer cells with or without the destructive effects of the radiation released by the nuclide material activated at the site of the tumor by the same or additional neutron radiation beams to the cancer site. A charged particle beam of ions passed through the body of the patient to the cancer site simultaneously with the neutron beam used to destroy and/or activate the nuclide material at the cancer site, may also be used to cooperate with the radiation generated by the nuclide or applied per se in destroying cancer cells in a medical procedure in which the entire tumor is progessively attacked and destroyed, or a plurality of the sane or different tumors are so affected and destroyed or caused to regress or stop growing.

4. A computer may be employed, in the manner described, to control the generation, duration, intensity, tuning or frequency, focusing and/or relative scanning movement of the beam and body of the patient under treatment, in performing automatic radiation treatment and the destruction of cancer in a living being by the means described above employing a single beam of radiation, a plurality of the same or different beams of the type described or one or more of the radiation techniques described including nuclide released radiation. Computer controlled scanning movement may be effected by controlled beam deflection per se while the patient is strapped and held stationary, motorized multi-axis deflection of the beam generator itself and/or computer control of the operation of two or more motors operable to drive the table or platform supporting the patient with respect to the beam apparatus as provided, for example in FIG. 1 of the drawings.

5. Treatment as described under the control of a computer may be effected by generating and applying feedback signals with sensors of the type described and/or by means of other sensing arrangements which signals are computer processed and analyzed to indicate the location, extent and condition of the tumor(s) and are employed to generate command control signals for controlling the operation of the one or more beam generating devices and/or the motors driving the patient support or beam device to effect controlled scanning movement during beam generation and treatment. The techniques for effecting automatic computerized image analysis illustrated and described in such U.S. Pat. Nos. as 4,600,086; 4,511,918; 4,338,626; 4,148,061 and 4,118,730 may be employed to generate control signals per se and/or in accordance with information provided from a memory defining a so-called expert system connected to and accessed by the main computer employed to automatically control beam generation, operation and scanning during a treatment operation. By employing such a computer and process for controllably applying radiation and scanning cancer tissue with destructive radiation to the exclusion of normal tissue adjacent the cancerous tissue, the volume of tissue within the patient's body containing such cancerous tissue may be so irradiated to the exclusion of surrounding tissue which may receive little if any destructive radiation, in an operation having the effect of progressively destroying the tumor or cancerous growth until its cells are all destroyed.

6. In yet another form of the invention, a television camera is supported by means such as shown in FIG. 1 and is operable under computer control to scan a select portion of the body of a patient, such as a portion of the skin containing a growth or tumor to be operated on and removed, and to generate an output video picture signal or signals which are computer processed and analyzed to generate control signals which are applied to control the surgical procedure. If such surgery is to be performed by means of a cutting tool such as a knife or rotary cutting tool supported by a manipulator, video signals derived from the camera or a plurality of television cameras, electro-optical sensors or the like, are computer processed and analyzed by means such as disclosed in U.S. Pat. No. 4,600,086 resulting in the generation of control signals which are applied to control the operation of the surgical tool and its manipulator to cause same to perform a select surgical operation, such as the removal of a tumor from the skin or beneath the surface of the skin after an initial incision has been made to expose same. Such command control signals may also be operable to control the operation of auxilliary device(s) such as drug and fluid administration means, suction means for removing body fluid, blood and severed tissue, etc. to successfully perform the operation in accordance with information derived from the computer's memory or an auxilliary expert system addressed by signals from the computer.

Modifications to the medical electronic system 10 and the apparatus illustrated in the drawings and hereinbefore described for performing continuous diagnosis and/or treatment of a malady in a living being are noted as follows:

1. Computer controlled image analysis techniques, such as defined in my copending application Ser. No. 07/609,917 filed Nov. 5, 1990 and in copending application Ser. No. 07/402,991, may be employed in the electronic circuitry of the computer 60 or CPU 112 to automatically detect and locate one or more malignancies, tumors or other abnormal growths or scar tissue on skin or tissue beneath the skin such as in various organs or bones of a living being. As indicated above, the image information stored in memory 130 or other memory is automatically processed and analyzed by the computer to determine the location and extent of a tumor or tumors as described wherein coordinates and density of the tumor and surrounding body tissue are calculated based, for example on the result of analyzing the image information derived from one or more computerized axial tomography scans of a select portion of the body of a living being supported on table 25. The resulting computed coordinate information codes may be applied to control the operation of one or more surgical dedevices such as a motor operated cutting tool, a radiation generating tool or tools or other form of tool and one or more manipulators for such tools and/or for tissue to be operated on.

One form of surgical device is a surgical laser, such as a carbon dioxide, argon or excimer laser, one or more of which may be secured to or movable on a support such as the frame or arcuately shaped support 16 or a carriage which is motor driven back and forth on a track supported by such support or an automatic manipulator supported thereby or any other portion of the assembly 15. Other forms of radiation beam generating devices known in the art which will generate and direct surgical treatment or curative penetrating radiation along an axis may be similarly supported and controllably operated to effect automatic surgery with respect to select tissue, such as tumors and the like, scar tissue, lesions or other maladies requiring surgery, curative or corrective action attainable by controlled radiant energy such as beamed or focused radiation. Mechanical surgery, and/or the controlled application of select chemical or biological agents to select tissue of the living being may also be effected under the control of command control signals generated by the computer as described to remove or beneficially treat injured or diseased tissue or prepare same for additional treatment.

2. In addition to the use of an automatic manipulator supporting an electromechanical surgical cutting tool or tools and, in certain instances, an automatic manipulator for body tissue to be operated supported by the assemly 15 or frame 16, one or more manipulators for a device or devices for applying a select quantity or quantities of one or more medical materials or drugs may be similarly supported and manipulated under the control of command control signals generated as described by the computer after electronically processing and analyzing the body scanning signals. Such command control signals may be employed for example, to control the operation of a manipulator for an injection device, such as a hypodermic needle or tool which is operable to penetrate a select portion of the body of a living being predeterminaly located on the table 25. The penetration depth of such tool or needle is predeterminately controlled to terminate the end of the tool adjacent or within select tissue whereafter a select amount of medical fluid is ejected from the open end of the tool into or adjacent select tissue such as a tumor under the control of the computer.

The movement of the electromechanical surgical tool or the operation of the manipulator therefor and the operation of the tool on select tissue are controlled by command control signals generated by the computer in analyzing the described image signals prior to start of the surgical procedure and/or during such procedure. A combination of laser and electromechanical surgery with or without the controlled application of a drug or drugs as described, may be employed to treat certain medical conditions such as the destruction of tumors, scar tissue, lesions or the like and/or the transplanting of organs, organ tissue, or genetic material at select locations of a living being requiring select site preparation such as attainable by surgery or the like.

3. Corrective surgery employing an electromechanical surgical tool such as a rotary or oscillating cutting tool or knife per se or in combination with surgical radiation such as a beam of intense light generated by a laser operable to cut, vaporize, burn, heat other otherwise affect select tissue, may also be employed to prepare a site in the body of a living being to receive a transplant such as an organ, select tissue or cells, select drug units or a drug dispensing device in accordance with command control signals generated as a result of computer analysis of image and/or spectral signals generated by one or more sensors of penetrating and reflecting radiation scanning exposed tissue of a wound or incision and, in certain instances, penetrating X-radiation, ultrasonic radiation, nuclear radiation and magnetic resonance or spin radiation generated, for example, by nuclear magnetic resonance image information generating apparatus of conventional design.

4. Apparatus of the type disclosed above may also be modified to employ optical fibers or the like to conduct either or both tissue penetrating inspection radiation in its premodulated and/or post modulated condition and/or surgical radiation to select tissue of the body of a living being. A fiber bundle or light pipe may be disposed in a rigid tube or needle or a flexible tube such as a catheter, either of which is either inserted into select tissue or a cavity by an attendant medical person and/or is predeterminately manipulated by an automatic manipulator controlled by command control signals generated as described to dispose its operating end or head at a select location or locations in the body prior to and/or during the operation(s) of the surgical tool and/or one or more drug or medical material administering devices. In other words, the entire medical procedure may be controlled, as described, by a computer, or a select part of such procedure may be controlled by computer while one or more portions of such procedure may be effected by a person such as a surgeon or nurse.

5. To effect certain surgical operations on select tissue located beneath the surface of the skin or within the body of a living being, one or more tissue manipulators may be supported om a common mount such as a manipulator arm or carriage which also supports the surgical tool or a group of surgical tools which are operable to perform different functions in the same or different surgical operations. Such tissue manipulator or manipulators may be automatically operated under the control of select command control signals generated by the computer in analyzing the image and/or spectral information signals derived from radiation scanning select tissue prior to and/or during the performance of the operation. Such tissue manipulator may be constructed and automatically controlled in accordance with the teachings found in my copending patent application Ser. No. 249,404 entitled Automatic Manipulation System and Method and in my U.S. patents Re: 26,904; 3,259,958 and 3,412,431 as well as the reference patents thereof and may include one or more operating heads which are carried by respective manipulator arm assemblies and contain one or more grippers and/or suction devices for gripping and/or retaining by suction a select portion or adjacent portions of tissue during the initial stages of the operation and controllably holding and moving such tissue as the operation proceeds in a manner to permit the surgical device to initiate and continue its operation. With such an operating arrangement, the computer is programmed and adapted to automatically control a plurality of power operated devices such as motors, solenoids and/or fluid operated actuators to predeterminately locate the surgical tool or tools with respect to the living being strapped to table 25, move and operate the tissue manipulator to engage and grip or suctionally hold select tissue adjacent the area of tissue or skin to be initially operated on, controllably operate the surical tool and the motors driving the tissue manipulator or manipulators to hold and controllably move tissue adjacent the incision as the operation proceeds to open the surgical wound and/or otherwise move tissue being operated on to facilitate and effect the desired surgical operation or other teatment such as a corrective or curative surgical procedure.

If the surgical procedure is one in which a tumor beneath the surface of the skin or wall of an organ is to be destroyed or select tissue beneath the surface is to be operated on, the surgical tool may be computer controlled in its operation to form an incision at a location aligned with the tumor or internal tissue to be operated on as determined by computer analysis of the modulated penetrating radiation sensed information signals and the command control signals generated by the computer and applied to the tool manipulator, the tool and the tissue manipulation device. The same surgical tool and/or an auxilliary tool is further controlled thereafter by further computer generated control signals applied to the tool and its manipulator to advance the tissue cutting action to the site of the tumor after which the same surgical cutting tool continues its cutting operation and is manipulated by its computer controlled manipulator to destroy the tumor. In the alternative, an auxilliary power operated knife, rotary cutting tool, laser or other form of vaporizing abrading or burning radiation beam generating device may be automatically manipulated to direct and controllably move its scanning axis by such computer generated signals which also control the operation of the radiant energy generating device to cause its radiation beam to penetrate and controllably operate on select tissue such as tumor tissue and a select amount of adjacent tissue to the exclusion of other surrounding normal tissue.

6. As indicated above, the computer controlled surgical tool may comprise a surgical laser which generates and directs its collimated operating laser light beam through space to the tissue it is intended to vaporize, ablade or burn. In a modified form, such laser light may be directed along a light pipe such as the interior of a narrow hollow stainless steel tube or hypodermic needle, an optical fiber or fiber bundle or the like extending along such tube, a catheter or a tube of a laparascope which is inserted through an incision in the skin or the wall of a body duct by a surgeon or by an automatic computer controlled manipulator as described above to dispose its operating end in alignment with the tissue or bone to be operated on thereby. In a modified form of the invention, inspection light is generated and directed along such a tube or a light pipe therein and from the end of the tube to intersect select tissue during movement of the tube through the body to generate and reflect inspection light from tissue at the end of the tube which reflected light is passed back through the tube or a light pipe therein to a photoelectric detector, detector array or a television camera. The resulting image signals are computer processed and analyzed as decsribed and electronically compared with signals recorded in or reproduced from memory to generate control signals for controlling the operation of a motor or motors driving and manipulating the tube or laparascope to a select location and automatically operating a rotary cutting tool, oscillating blade cutting tool at the end of the tube and/or a surgical laser to cause select tissue, such as a tumor, to be destroyed, severed or otherwise operated on.

7. As a supplement to the medical procedures and apparatus described above, the image signal analyzing computer may also operate to analyze spectral information per se or as a supplement to the image information generated by one or more of the described inspection radiation generating and scanning devices such as the described neutron beam scanning system, computer axial tomographic (CAT) scanning system, nuclear magnetic resonsance system, photoelectrical detection system for reflected radiation or the like, spectral radiation generated when pulses of laser radiation are caused to intersect tissue and/or body fluid may be detected by suitable electro-optical or spectral detection means supported by the operating head of the tool or coupled to a light pipe terminating at a select location on or adjacent the operating head to receive such spectral radiation. Such pulses or spectral generating radiation may be generated by a laser which is either predeterminately located on the operating head of the described surgical tool, adjacent thereto or remote therefrom wherein the beamed output of the laser is directed by optics such as a mirror system or light pipe to receiving and directing optics at or adjacent the tool head to be passed thereby to tissue aligned with the tool head or at the end of the tube or hollow needle defining the laparascope or catheter or other instrument. Depending on the malady being operated on or corrected, either or both the spectral and image or reflected radiation defining information signals may be analyzed by the computer to permit it to detect select tissue or cells in the body and automatically determine and indicate the extent and location thereof in a manner whereby control signals of the type described are generated and applied to subsequently control one or more surgical tools of the types described to cause them to perform a select operation or corrective procedure on select tissue.

For additional information and details of spectral or spectrographic information generating means involving the use of laser light energy, reference is made to my copending patent application Ser. No. 07/640,023 filed Jan. 11, 1991 and entitled MEDICAL TESTING APPARATUS AND METHOD.

As indicated above, spectral information may be correlated with select tissue, such as tissue of a growth or malignancy requiring removal or radiation treatments and may be utilized per se or in combination with image information generated as described to control a laser to generate one or more pulses of tissue or cell changing or destroying radiation a spectral radiation detector detects same and generates variable or analog spectral defining signals which are analyzed by the computer to generate the described laser control signals to cause the laser to generate a pulse or pulses of cell changing or destroying radiation upon detecting the presence of select cells such as cancerous cells.

Additional features and modification to the described drug compositions and methods for producing and applying same are noted as follows:

1. For the treatment of cancer, antibodies, such as monoclonal antibodies which are marker specific, may be produced by conventional methods known in the art wherein such antibodies or antibody fragments are targeted to a specific carcinoembryonic antigen (CEA) and are bound to any of the described killer cells, biodegradeable or dissolvable coatings thereon or microcapsules containing one or more of such lymphocytes, macrophages or the like or time release containers for same.

2. Various biodegradeable or body fluid dissolvable organic and inorganic polymers may be employed for the described lymphocyte or killer cell coating and encapsulating materials, such as described in U.S. Pat. No. 4,434,153 which discloses which discloses various waxes, cellulosic materials polyvinyl polymers and the like which will dissolve or biologically degrade to destroy encapsulation and release their contents at times which may vary from minutes after initial injection or exposure, to hours thereafter, depending on the coating or encapsulation material and its thickness. Polymers for forming such coatings and microcapsules are described in such U.S. Pat. Nos. as 3,811,444; 3,867,519; 3,888,975; 3,971,367; 3,993,057 and 4,138,344.

3. In a preferred form of the embodiments defining drug units, such as those illustrated in FIGS. 9, 11, 12, 13, 17 and 18, the average maximum dimension or diameter of the drug units is preferably in the range of four to ten microns which will permit the drug unit to flow through capillaries. Larger diameter drug units may be produced to flow through blood vessels or to be disposed directly in tumors by needle or surgery.

Figure 19:
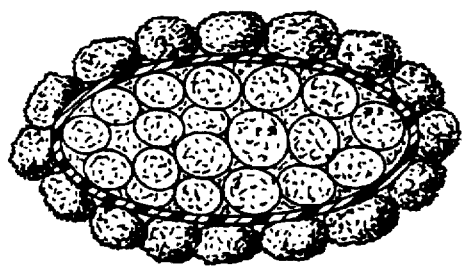
Figure 20:
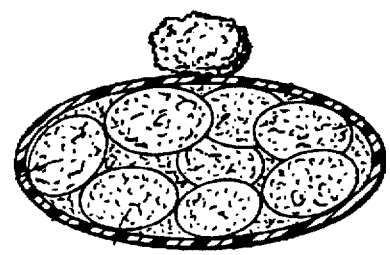

4. The drug units illustrated in FIGS. 18, 19 and 20 may contain a number of biological units of the same or different types including antibodies, activated lymphocytes, antibiotic and anti-viral agents as well as one or more chemicals for cooperating in the treatment and destruction of a cancer or tumor to which the drug units target.

5. The drug unit embodiments illustrated in FIGS. 11, 12, 15, 18, 19 and 20 may be fabricated with a chemical contained within the microcapsules thereof, which chemical serves to react on the wall of the microcapsule or vesicule of the unit and to dissolve, biodegrade or render such was porous a time delay after formation of the drug unit sufficient to permit it to be administered to a patient and permit the drug unit to become targeted to a specific disease site, such as a tumor or malignancy.

6. In the embodiments illustrated in FIGS. 12, 13, 17, 18, 19 and 20, the drug units may be constructed such that, when targeting of the antibody portion takes place, physical separation of the killer cell from the antibody takes place when the microcapsule containing one or more of such killer cells is weakened permitting it to be opened thereafter by internal pressure, biodegradation or physical and/or chemical activity associated with the contents thereof. If the antibody itself is operable to attack the cell of the antigen to which it is attached, its activity in attacking such cell may be such as to cause it to detatch itself from the surface of the killer cell or the microcapsule therefor and, in so doing, to provide an opening across the portion thereof to which it was attached to permit the contents of such microcapsule to be released at the site of the antigen to permit the lymphocyte(s) to attack one or more cells in the vicinity of their release.

7. In any of the embodiments illustrated in the drawings, a biodegradeable bioadhesive may be applied to the surface of the microcapsule, the biodegradeable coating on the killer cell or activated lymphocyte or a plurality of same bonded to a capsule or liposome for bonding same to tissue at the site to which they are disposed or targeted. Such bioadhesive may also be contained within one or more biodegradeable microcapsules to be released therefrom upon biodegradation or dissolution of their container(s) at the targeted site so as to bond the drug units or the killer cell portions thereof to tissue at the site until such microcapsules containing the killer cells biodegrade to release same therefrom.

8. The drawings provided herewith are not necessarily drawn to scale nor are the relative sizes of the components necessarily shown to the same scale.

9. In the embodiments of the invention illustrated in FIGS. 9, 11, 12, 17, 18, 19 and 20, the microcontainers or microcapsules employed to encapsulate the one or more phages, lymphocytes or similar chemical and/or biological unit or units useful in destroying or weakening cancer cells to which they are targeted or disposed next to, may be made of cells from living tissue or blood, such as red blood cells and/or other cells which have been biologically engineered as a result of gene splicing and the like and grown by incubation or other means outside of the body.

10. In the embodiments illustrated in FIGS. 17–20, the antibody or antibody fragments 76 may be bound to the microcapsule and the latter may be so constructed that, when the antibody targets or attaches itself to an antigen, such as an antigen of or associated with a cancer cell or cells, it weakens the microcapsule wall, creates an opening therein or ruptures same permitting the contents thereof to be freed from encapsulation and the killer cells and/or other biological or cemical elements contained therein to be dispensed adjacent to or against the cancer cell or cells for weakening or destroying same.

11. The techniques previously described, such as illustrated in FIGS. 1. and 2, may be employed for penetrating, weakening, boring a hole in or rupturing the coating, liposome or microcapsule surrounding the killer cell or cells at the site of the cancer.

12. The methods described in U.S. Pat. Nos. 4,310,506 and 4,448,765 may be employed in the production of micrcocapsules such as liposomes containing killer cells and the likes as illsutrated in FIGS. 9, 11, 12, 17, 18, 19, and 20.

13. In a modified form of the invention, drug units may be formed which may be administered in select doses to the bloodstream of a living being for the purpose of removing a blood clot or clots constricting or blocking a blood vessel, such as an artery, vein, capillary or aorta when units thereof target to such blood clot matter. Such drug units may be fabricated of one or more of the biological targeting particles described above, such as a monoclonal antibody which is bioengineered to attach to blood clot material in the body of the living being to whom the dose of drug units is administered or injected, and a quantity of blood clot dissolving matter which is preferably encapsulated within a microcontainer, such as a microcapsule, liposome or biodegradable or dissolvable material which degrades or dissolves under the effects of body fluid such as blood. The degradation or dissolution of such matter containing the blood clot dissolvant is preferably such as to allow most or a sufficient quantity of the drug units of the dose to target to the material of a blood clot and to release the dissolvant or clot degrading contents against the clot in a manner to dissolve or destroy same sufficiently to permit the remaining clot material to detatch from and be carried with the blood for disposal from the body by natural means without inflicting damage to the circulatory system. A suitable antibody for use in such drug units is an anti-fibrin antibody targeted to the fibrin of the blood clot of the living being to whom the drug dose is administered while the clot dissolving material contained in the drug units and targeted thereby to the blood clot to be destroyed comprises a clot fibrin dissolving drug such as a small quantity of streptokinase contained in encapsulation in each of the drug units of the administered dose. In a preferred form of this embodiment of the invention, the encapsulating container for such blood clot dissolvant is operable to dissolve or degrade under the action of the blood at a time after injection or release of the drug units to the bloodstream such that (a) a substantial quantity thereof will have had time to target to the blood clot or clots being treated and (b) those drug units which have not so targeted will have time to be excreted from the body to avoid excess bleeding due to the clot dissolving drug and to reduce the possibility of allergic reactions thereto. Furthermore, by so delaying the release of the fibrin dissolving drug from the drug units, antibodies which may be present in the living being under such treatment and which would normally inactivate some of the streptokinase will not be effective in causing such deactivation and will not blunt beneficial response of the drug.

Another medical material or drug which may be encapsulated and fabricated into drug units of the type described for treating or dissolving blood clots is biologically engineered tissue plasminogen activator (t-PA), the side effects of which (e.g. bleeding) may be greatly diminished by delivering and releasing small amounts thereof from each drug unit directly at the site of the clot to which the drug units are targeted by, for example, the respective anti-fibrin antibodies which form the drug units.

15. In the embodiments described above which define monoclonal antibodies targeted to select cells in a living being and biodegradeable or dissolvable microcontainers for a chemical or biological material operable to react on select cells or clot material, small quantities of inactivated solid adhesive or liquid adhesive may be disposed in separate microcapsules of the types described which are attached to the drug units and are operable to degrade or dissolve under the effect of body fluid and release such adhesive after targeting to such select cells or clot material so as to bond the capsule containing the drug to the targeted material so that it may itself dissolve or degrade thereafter and release it contents to the adjacent material to which it is so bonded.

16. Drug units of the types described above may be formed of biologically engineered materials such as select monoclonal antibodies or the like and respective encapsulated small quantities of tissue growth factors, such as epidermal growth factors (EGF) for use in promoting the healing and growth of select tissue in living beings. For example, a select antibody may be cloned and manufactured as a quantity of monoclonal antibodies targeted to select matter, such as blood fibrin or select healthy cells of a select organ of a living being under treatment. Drug units formed of one or more of such antibodies and a small quantity of select tissue or epidermal growth factor, which is contained or encapsulated as described in a microcapsule for delayed release therefrom at the targeted organ or wound, may be administered to the body as a dose for treatment of such maladies as (a) the healing of an internal wound caused by surgery or other means, (b) the growth or generation of tissue of a deficiently grown or underdeveloped organ, (c) the growth of tissue of an organ or portion of the body which has been depreciated or partly destroyed by disease, such as after the disease has been cured or forced to stop or regress, such as cancer or (d) the regrowth or regeneration of an organ, gland or other tissue at the site it previously existed. Such treatment may involve injection of a select amount of such drug units into the bloodstream of a patient, the majority of which units are allowed to target to a select site in the body, such as a select organ, wound tissue or portion of an organ or duct from which a tumor has been removed by surgery or by treatment with drug units such as described above. After targeting to the select site or sites in the body, the targeted drug units simultaneously and/or at different times, release their respective small quantities of tissue growth factor(s) which flow directly into the tissue against which the drug units contain-same are disposed, and serve to promote and effect the growth of new tissue and/or healing of weakened or wound tissue to which the medication flows.

17. Additional modifications to the drug units described above are noted as follows:

a) Combinations of two or more chemical and/or biological medication or agents may be combined as small quantities thereof in the same microcontainer forming the drug unit to be simultaneously released therefrom to tissue to which such drug unit is targeted and to simultaneously flow to the adjacent cell or tissue to respectively react thereon for destroying the cell or cells affected thereby, if cancerous or precancerous, or for otherwise treating same such as such as by stimulating or repressing cell growth, healing wound tissue, controllably altering the cell genetic material, destroying, scavaging or repressing select contents of the cell or effecting the growth of new cells.

b) Treatment doses of the drug units described herein may be composed of two or more different chemical and/or biological agents, in the same or different microcontainers of the types described, each targeted to the same body matter or cells, wherein certain of such containers are fabricated to release their drug contents at different times after targeting so as to prolong the treatment and the action of their contents over an extended period of time. Doses formed of drug units containing the same chemical and/or biological agent may be similarly produced to release the contents of their microcontainers at the targeted site over and extended time interval.

b) Two or more chemical and/or biological agents of the types described or of other types, may be respectively disposed in microcontainers which biologically degrade or dissolve at different times after being injected into the body, one of which is operable to effect a first treatment function with respect to the tissue of the targeted site, such as the destruction of cancer cells thereat, when first released from encapsulation, whereafter the one or more additional agent(s) may be released thereafter to effect advancement or completion of the combined treatment, such as by continuing same in a different manner and/or healing or growing tissue at the site of such treatment.

Such treatment may be performed without resort to surgery by targeting and releasing one or more chemical and/or biological agents in sequence as one or more doses thereof to a malignancy such as a discrete tumor or group of tumors at a site of group of sites in the body and sequentially releasing each or groups thereof by the timed biodegradation of the microcontainers so targeted until remission or destruction of the malignancy(s) is attained, after which one or more subsequent doses of drug units are administered, which contain quantities of one or more tissue repair and growth factors which operate to repair tissue damaged by the first phase of the treatment and stimulate or effect the growth of new tissue to replace the damaged or destroyed tissue and effect healing at the site of the malignancy. Treatment of a tumor may be started by targeting drug units containing one or more cell killing chemicals released against the tumor to which they are targeted, followed by targeting in the same or additional doses of drug units containing one or more biological agents such as suitable white blood cells such as macrophages, lukecytes, T-cells and the like which operate to complete the destruction of the tumor(s), followed by the application of drug units, in the same or in additional doses, containing one or more tissue repair and/or growth factors.

18. By incorporating a small amount of a radioactive tracer material in all or certain of the drug units, such as in the drug or active element thereof, an electronic sensing and imaging system may be employed to view not only the concentration of the targeted drug units at the targeted site but also the therapeutic effects (e.g. destruction or remission of the malignancy) of the drug(s) released therefrom at the site(s). Such electronic imaging may be employed to indicate to the person(s) effecting treatment, how to continue and complete the treatment.

19. In still another form of the invention, tissue cells similar to those normal tissue cells at the site of said cancer, are either obtained from another site of the body of the living being under treatment or are biologically engineered and cloned from cells of said living being and are mixed with an epidermal or tissue growth factor which may also be manufactured by genetic engineering and cloning same from similar material of the same or other living being and applied, as described or otherwise to wound tissue or other tissue for effecting a select tissue healing and growth function at a select site in a living being.

Modifications to targeting drug units described above and the methods for employing same to prevent, cure, limit and/or detect disease in the body of a living being which define additional embodiments of the invention are noted as follows. Reference is also made to such U.S. Pat. Nos. as 4,674,480; 4,665,897; 4,764,359 and 5,017,379 for additional details of drug units and methods for employing same to target specific drugs to select cells of a living being for purposes other than claimed herein.

Drug units formed of small quantities of various chemical and/or biological materials and one or more targeting elements, such as a monoclonal antibody, fragment of same or other biological element shaped to target and bind itself and the drug unit to which it is bound or is contained to a select group of cells of the body of a living being under treatment, may be administered by ingestion or injection in select quantities or doses thereof to a living being. Upon targeting and binding to select tissue or blood cells, such units may be thereafter operable to release their small quantities of drug in the vicinity of or against the cells to which the drug units are bound whereafter the drug or medical material carried by the drug unit enters the adjacent cell or cells to which the unit is targeted and operates thereafter to beneficially affect the cell mechanism or destroy the cell depending on the results required of the treatment. In one form, the drug may render the cell susceptible to further treatment with a drug, chemical or radiation. In a second form, the drug may flood the cell and restore the regulatory apparatus of the cell to cause it to mature naturally by overcoming or supressing a genetic flaw in the mechanism of the cell. In a third form the drug may promote normal or beneficial growth of the cell. In a fourth form the drug may destroy the cell. In a fifth form of the invention, the drug released from the drug units to the select tissue or blood cells may operate to destroy, regulate or render inactive certain disease defining matter, such as virus which live and/or multiply within the cell. The drug or drugs may also perform a plurality of such functions.

In yet another form of the invention, drug units to be administered in select quantities or doses to a living being by ingestion or injection through the skin or by catheter injection means, may be formed of a targeting element such as a monoclonal antibody, fragment thereof or other biological material externally shaped and disposed to target and bind to a select body cell and a small quantity of a drug which is operable to enter the cell to which the drug unit is targeted. Such drug, after entering the cell to which the unit is targeted and/or one or more cells adjacent thereto if so operative, may react on the cell in one or more ways as described. One reaction may be to destroy or degrade the cell. Another may be to render the cell susceptible to further treatment with additional drug material and/or by biological material such as cells of the immune system. A third may be to stimulate growth of the cell such as by employing a suitable growth factor as or part of the released drug from the drug unit. A fourth may be to achieve cell differentiation by affecting or controlling the genetic or other cell regulatory apparatus so as to allow the cell to mature normally allowing the cell to perform its proper or normal functions. The drug, for example, may comprise a derivative of vitamin A, such as a synthetic retinoid or retinoic acid and may be delivered by targeting the drug units containg same to immature white blood cells having a genetic flaw which disrupts the cell's control mechanism to cause leukemia to develope. When so targeted and caused to flood such cells upon release from the drug units, the retinoid achieves differentiation forcing the cancerous or precancer cells to develop into normal cells and become incapable of abnormally dividing.

In one method of treating a disease in a living being, such as leukemia, such units are produced in quantity each of a targeting element or elements and a small quantity of a retinoid or similar acting drug or a combination of a retinoid and other drug which cooperates therewith in cell treatment, and such dose is adminstered periodically by ingestion and/or injection to a living being a detected precancerous or cancerous condition, to become targeted to the select immature or cancer cells. The drug or drugs of the drug units described which are operable to beneficially affect the cell mechanism, destroy or render harmless certain harmful contents of the cell such as disease defining virus or other biological or chemical elements, may be bound per se to the drug unit or encapsulated within a body fluid dissolvable or biodegradeable microcapsule such as a liposome or a container made of a biodegradeable polymer as described and fabricated in accordance with the teachings of my U.S. Pat. No. 4,674,480 and the literature listed therein.

Figure 9:
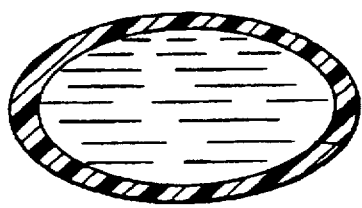
FIGS. 9–20 show embodiments defining drug units for treatment.
Figure 10:
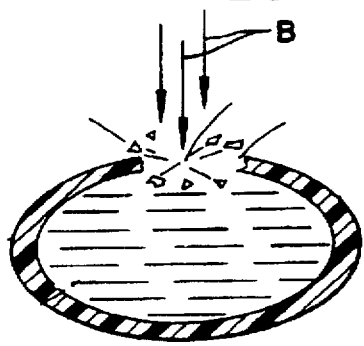
Figure 11:
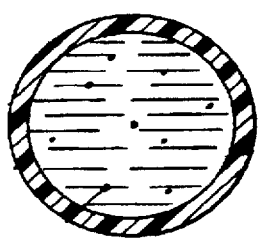
Figure 12:
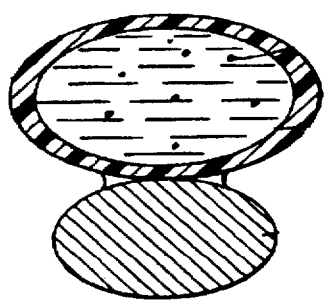
Figure 13:
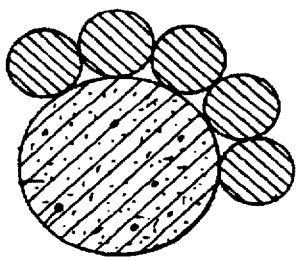
Figure 14:
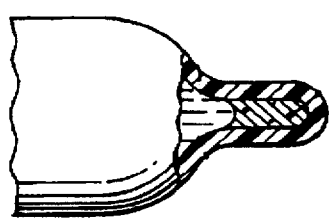
Figure 15:
Figure 16:
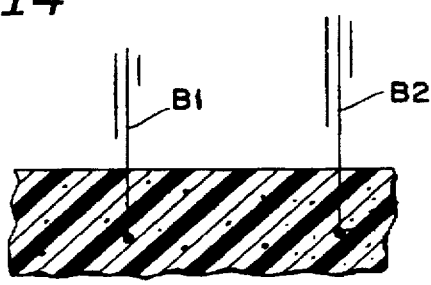
Figure 17:
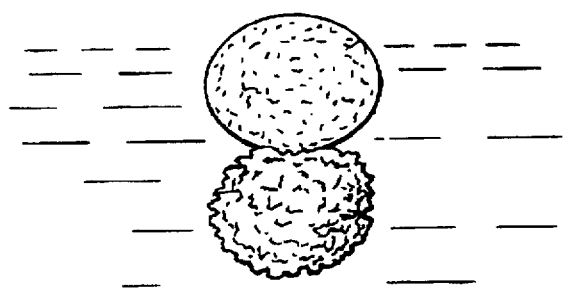
Figure 18:
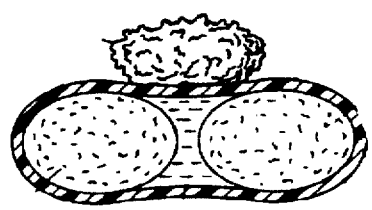

The drug units described above which contain quantities of one or more drugs which control the growth regulating mechanism, genetic structure and/or the growth or harmful effects of foreign bodies or matter within the cell or prevent such from entering the cell when such drug or drugs are in the cell, may be structured in accordance with the teachings of FIGS. 9 and 10 of my U.S. Pat. No. 5,017,379 and the descriptions thereof and may be produced in accordance with the teachings of my said other patents in this field described above, such as U.S. Pat. No. 4,655,897. Such drug units may contain a single or a plurality of cell and/or cell contents modifying, limiting and/or destroying drugs to perform multiple functions such as the destruction or neutralizing of chemical or biological agents such as harmful virus within the cell and the regulation, enhancement or suppression of cell development or growth.

Such cell regulating drug units may also contain or be combined with other drug units targeted to the same cells or same group of body cells and containing a medical material or materials operable to have different effects on the targeted cells. Such different drug units may be mixed with each other to form a single dose or group of doses or may form separate doses each of which doses are administered to the body or blood of the patient at a different select time interval in accordance with a predetermined treatment procedure operable to treat or cure a disease, group of diseases, deficiency or group of deficiencies in the body of a living being.

In a particular form of drug unit and method of treatment of disease, the targeting elements of the drug units may be designed to bind to select infected tissue or blood cells such as cells containing the HIV or AIDS virus which mature and multiply therein. The drug of such drug units may comprise one or more biologically engineered and produced natural and/or synthetically produced medical materials designed to effect one or more of the beneficial functions of destroying, regulating or stopping the growth of foreign disease defining or disease causing matter in the cell, such as the HIV virus or other virus, chemical or biological element which defines or causes a disease. Once such drug or mixture of drugs enter the cell after the drug unit or units in which the drug or drugs are contained, one of such therapeutic, curing or cell killing action is effected thereby. The medical material carried and targeted by the drug units, for the treatment of diseases such as acquired immune deficiency syndrome or AIDS may comprise one or more of such drugs as aziodothymidine (AZT) or other drug which stops the HIV virus from reproducing within the cell the drug targets to and enters; genetically engineered, produced and killed virus such as derived from the HIV virus or other vaccine active against the AIDS causing or HIV virus within the cell.

For the destruction or control of certain types of tumors and cancers, the drug contained in or defined by the described drug units which are targeted, as described, to select tissue or cancer cells in the body of a living being, may comprise a tumor necrosis factor (TNF) biologically produced from antitumor substances made by body cells. Upon becoming targeted to and after entering select body cells such as select tumor cells or select precancerous cells such tumor necrosis factor operates within the cells it enters to destroy them if they are cancerous, restore them to benign or normal cells or, in certain therupeutic operations, to protect the entered cells from viral or chemical invasion and destruction or disease causing effects by certain viruses.

In yet another embodiment of the invention, the drug or drugs targeted by the drug units to select cells and thereafter caused to enter such select cells may be derived and genertically engineered from natural substances, such as human saliva of a healthy person from which such drug has been derived and produced in quantity and combined as taught in my said parent and previous patents with targeting material to form the described drug units to block viral reproduction, such as the HIV or AIDS virus within the targeted cells. If such viral reproduction drug is combined with a drug operable to kill the small number of disease causing or defining virus that may enter the targeted cell, it may more easily treat the disease and prevent its spread by killing the few virus which enter the cell but are blocked from rapidly multiplying therein by the drug which blocks viral reproduction within the cell.

In still another embodiment, the drug or drugs of the drug units may comprise or contain suitable growth promoting protein or proteins such as a select tissue growth factor and, in certain arrangements, one or more specific tissue cells, operable to effect the growth and multiplication of quantities of tissue at select body sites to repair damaged tissue and organs of the body or, in certain instances, to grow new organs. The targeting elements of such drug units may be designed and shaped to target same to select body cells such as the tissue of select organs. Upon release of the tissue or cell growth factor at such select organ and tissue site to the healthy cells thereof, the growth factor drug serves to cause the cells thereat to multiply and grow new tissue to replace aged, destroyed or diseased tissue. Such procedure and drug administration may be effected after a disease curing or supressing operation as described and/or after a physical tool, radiation or chemical operation to destroy and remove diseased and scar tissue and/or aged or worn tissue to be replaced with the newly generated tissue grown as a result of proper application or applications of one or more doses of one or more growth factors to the select site or tissue of the body.

In still another form of the invention various other drugs may be targeted per se or in combination with one or more of the described drugs in the same or different drug units to treat specific cells prior to and/or after treatment with one or more of the hereinbefore described drug units and the drugs released thereby at the targeted cells to enter and beneficially affect same such as by regulating cell function, destroying or stopping the growth and spread of foreign bodies such as virus in the cells and/or stimulating the cell mechanism to destroy, stop the growth of and/or prevent such virus from penetrating the cell wall and escaping the cell. Opportunistic infections such as toxoplasmosis and pneumocystis pneumonia may be treated along with cells infected with the HIV or AIDS virus by targeting drug units containing one or more drugs which are destructive of the organisms or infectious material defining such infections to specific body cells or sites containing such cells and releasing such drugs as pyrimethamine and sulfadiazine to treat toxoplasmosis and trimethoprim and sulfamethoxazole for pneumocystis pneumonia at the targeted site prior to and/or after the described targeting and treatment of the AIDS virus infected cells. An antibiotic, such as clyndamycin and an antimalarial drug, primaquine, may also be so administered and delivered to treat the PCP pneumonia infection prior to and/or after treatment of the cell virus infection as described. Delivery of such drugs to select cells or tissue sites may be effected by incorporating small quantities of one or more of such drugs in targeted drug units by the means and methods described above and in my parent patents and applications as set forth above and administering select doses of such drug units in one or a select number doses as described.

The drug units described above and employed to destroy or beneficially affect select tissue or cells to which they target may also contain small quantities of short life radioactive material such as a radionuclide or a normally nonradioactive nuclide such as boron 10 as taught in my U.S. Pat. Nos. 4,665,897 and 4,674,480 to provide atomic radiation for supplementing the described drug or drugs in treating or destroying select malignant or infected cells or select contents thereof such as infectious virus in the cell and/or for providing detectable levels of radiation at a disease site or tumor, the detected level of which is an indication of such variables as the density of the drug units targeted to the site, the density or approximate quantity of infected cells and corresponding indications of the effects of such treatment with time. The quantized results of such radiation detection from within or exterior of the body may be employed to determin the quantities of drug units defining the dose or doses thereof and their frequency of administration to the patient to optimize the results of treatment and cure a disease or malignancy. Such detection signals may be computer analyzed to provide control signals for an intelligible indicating means such as a display and/or to control a means for automatically administering select quantities of select drugs and/or drug units or doses thereof at select times during treatment of the disease or malady.

In other embodiments of the invention, drug units of the types described may be operable to deliver select small quantities of gene altering drugs to select cells to which they are targeted to cause the cells to function normally, prevent disease defining virus from entering the cells and/or repress or destroy such virus. Such cells may also be conditioned by such drug or drugs to repair itself, supress or negate the effects of chemical polution of the cell and its mechanism and replenish or stimulate its means for producing select proteins needed for the cell to function properly and fight disease. The drug may also operate to reject the entry of virus or other disease elements into the cell or condition the cell by altering its genetic structure to effect such rejection.

A hereinbefore described, the drug units described above may be delivered to the body of a living being by injection of a dose thereof through a hollow needle such as a hypodermic needle, by ingestions such as by swallowing a cspsule containing same, from a body implant or a combination of such means. The implant may very from a biodegradeable implant implanted under the skin or otherwise retained in tissue or a body duct, which releases a steady of drug units with time as its wall or matrix degrades or dissolves with time under the effects of body fluid, to a more complex implant in a suitable housing containing one or more reservoirs of the same or different drugs or drug units. The drug mechanism of such implant may vary from a simple chemical, mechanical or electrical timer to one which is computer controlled. Such control may be effected by a computer external of the body transmitting timed control signals to a receiver or device in the implant to control the operation of a pump, pump motor, valve or valve actuator in the implant for effecting forced or gravity flow of select amounts of drug, drugs or drug units from the implant to the body or blood stream of the living being in which the implant is disposed. The computer may also comprise a microcomputer or microprocessor located in the implant which is preprogrammmed with a memory such as a solid state microminiature circuit read-only-memory or ROM and may contain a random access erasable memory or RAM for temporarily storing information signals derived from one or more sensors and, in certain arrangements, from signals, such as short wave or other signals, received from an external transmitter and computer outside the body.

A system and method employing such a computer controlled implant preferably employs one or a plurality of sensors of a physiological variable or variables, which sensor or sensors are connected to and/or supported by the housing of the implant and are operable to continuously or intermittently be energized and sense one or more body variables and provide the sensing signals generated thereby for computer processing and analysis. The computer may employ artificial intelligence and, in certain applications so-called fuzzy logic, as well as neural networking, to determine the presence and extent of select predisease and/or disease conditions or elements in the body by automatically processing and analyzing signals generated by one or more chemical, biological and/or electro-optical sensors sensing noe or more body fluids and tissue adjacent the sensor or implant. The results of such computer analysis are control signals to one or more controls for one or more pump motors or valve actuating device such as solenoids energized to effect controlled drug release from the implant reservoir or reservoirs by electrical energy generated by a battery in the implant. The sensor or sensors may be operable to sense and generate signals indicative of the presence of one or more disease precursors, disease indicating chemical or biological elements such as a specific protein or proteins, bacterium or bacteria or fragment thereof, fungus, virus or viral fragments. In addition to chemical and biological or bio-sensors, combinations of same with electro-optical sensing means operable to spectrally analyze light passed through an optical fiber and reflected from select tissue or body fluid such as blood may be employed as well as electro-optical sensing means sensing cell shape, size and color. If the latter is employed and defined by a photoelectric cell or an array thereof supported in or by the implant, image signal computerized analysis techniques of the types defined, for example, in my U.S. Pat. Nos. 4,969,038 and 4,653,109 may be employed using the on-board microcomputer to analyze electrical signals output by the photoelectric cell or microminiature array thereof in the implant when such photoelectric cells receive reflected or direct light from a light source in the implant directed at tissue or body fluid adjacent the sensor and/or implant. The results of such computer analysis of electro-optically generated sensing signals may determine by cell shape, color and surface texture analysis the presence and, in certain instances, condition of select cells, such as select cancer cells or other infected or diseased cells presence in the body fluid or fluids scanned. Such computerized image signal and/or spectral signal analysis may also determine the density of the select disease element, cell or virus in the body or fluid under analysis at any select time or times and may further determine time variations or trends thereof by means such as taught in my U.S. Pat. No. 4,653,109 entitled image Analysis System and Method.

The implant or other detection and control system, may also employ a combination of sensing means and subsystems employing electro-optical shape, surface texture and condition and color analysis of body fluid cells, virus, bacteria, fungus and fragments thereof as well the computer analysis of signals generated by one or more spectral radiation detectors, chemical and biological or protein detectors to automatically determine the presence, type and extent of a disease or disease elements in the body fluid or fluids sensed and to automatically control the administration of one or more drugs and/or drug unit doses to the body from the one or more reservoirs within the implant and/or located externally of the body. As indicated, such control is effected by computer generated control signals generated as the result of computer analysis of the sensing signals and applied to control the operation of one or more solenoids and/or miniature motors operable to control a valve or valves and one or more pumps for administering select amounts of fluid matter containing such drug, drugs or drug units to the body when predtermined disease or disease indicating conditions are detected.

In still another form of the invention, cancer cells may be detected in tissue and/or the blood of a living being in by an in vivo or in vitro scanning operation of the type described and may be automatically treated with a quantity of a drug to render same benign. Such detection may be effected when spectral radiation, such as spectral fluorescence, is generated when a laser beam is caused to scan and intersect blood and/or tissue cells of a select portion of the body of a living being by one or more of the means described above and such radiation is detected by one or more electro-optical or spectral sensors which generate output signals which are computer processed and analyzed. Coded electrical signals generated by the computer define characteristics of the spectral radiation detected and such signals are compared with coded spectral information which is recorded in memory and is indicative of the biological and/or chemical composition of cellular matter characteristic of a select disease or group of diseases such as defined by cancerous cells. If the result of such computer analysis indicates that spectral radiation is being generated as the laser pulse or continuously scans tissue or cells in the body or blood of a living being, a control signal or signals are generated and applied to control the application of a select quantity of a drug such a retinoid to the diseased or cancerous cell(s) scanned to render it benign. The drug may be administered as a fine particle such as a drop or drops of liquid or spray formed at a dispensing head supported by the carriage or manipulator supporting the laser or laser optics and directed therefrom along an axis to intersect the cell or group of cells detected as cancerous. The drug dispensing control signals may be applied to activate a valve solenoid, pump actuator or a magnetostrictive droplet forming transducer to form and dispense the drug in droplet form when living cancer cells are so automatically detected by a laser beam scanning device of the type described above. Auxilliary laser radiation may also be similarly applied to select living disease or cancer cells in vivo or in vitro to irradiate same and render them benign per se or in combination with the described application of a small quantity of a select drug, such as a synthetic or natural retinoid derivative of vitamin A which floods the cell or cells to which it is applied and forces them to mature to noncancerous cells.

In another form of the invention, a small quantity of a cell modifying drug, such as a retinoid, is controllably dispensed as as described from a nozzle or magnetostrictive dispensing device and applied to the radiation of a laser beam directed at a select cell or group of cells to receive the drug. The pressure of the directed laser beam is applied to the particles and impinges them against the cell or cells it intersects. A gas stream directed along the beam may also be employed to carry and impinge the drop or drops of drug so formed against the cell or cells intersected by the beam. The radiation energy of the laser light beam intersecting the cell or cells detected as cancerous may also be employed to heat or otherwise condition the cellular matter to render it more porous or otherwise receptive to the drug applied therewith. Where destruction of a diseased or cancerous cell or group of cells is desired, an auxilliary laser beam generating means may be pulse operated upon detecting such cancerous cell or cells as described and may direct a pulse of laser light of sufficient energy to intersect and destroy the cellular matter per se or in combination with a chemical or biological material applied therewith to such cellular matter simultaneous or sequentially with the beamed radiation. The combined effect of laser radiation and a select amount of controllably dispensed drug may also be employed to render select cancerous cells benign by means of the scanning and detection apparatus and method described above.

What is claimed is:

1. A medical radiation scanning system comprising:
   a) a first support,
   b) a second support movably supported by said first support and operable to be moved in multiple axis movement with respect to said first support,
   c) controllable motor means for reversibly driving said second support with respect to said first support,
   d) means for supporting a living being on said second support,
   e) means for retaining a living being substantially fixed on said second support as said second support is driven with respect to said first support by said motor means,
   f) a plurality of transducers supported by said first support and operatively disposed adjacent said second support,
   g) said transducers including first transducing means for generating and transmitting penetrating radiation in a direction of a living being supported by said second support and second transducing means for detecting radiation from said living being modulated with information derived when said penetrating radiation scans a select portion of said living being
   h) means for generating information signals on an output of said second transducing means in accordance with the modulated radiation generated by said second transducing means,
   i) a source of electrical energy for energizing said transducers,
   j) means for controllably operating said first transducing means in a manner to cause radiation to be generated thereby and directed at a living being supported by said second support and to scan a select portion of said living being,
   k) means for controllably operating said second transducing means to cause it to detect at least a portion of the radiation generated by said first transducing means after penetrating select tissue of the living being supported by said second support and to generate output electrical signals which are modulated with information relating to matter of the select portion of said living being,
   l) electronic computing means operable to receive the electrical signals output by said second transducing means, process and computer analyze same and generate coded electrical signals,
   m) means for applying said coded electrical signals to control operations of said motor means and said first transducing means to cause radiation generated by said first transducing means to scan and perform a select operation with respect to select matter in the body of said living being, and
   n) means for effecting a physical change in select tissue of a living being wherein said physical change affects the penetrating radiation detected by said second transducing means such that said physical change is represented in said coded electrical signals,
   o) means responsive to said coded electrical signals for controlling operation of said physical change effecting means in accordance with physical changes produced therewith.

2. A medical scanning system in accordance with claim 1 wherein said first transducing means is operable to generate beamed penetrating radiation at select tissue of said living being.

3. A medical scanning system in accordance with claim 2 including means for controllably moving said beamed radiation to cause it to scan select tissue of said living being.

4. A medical scanning system in accordance with claim 1 including means for focusing the penetrating radiation generated by said second transducer to a select depth within the body of a living being supported by said second support and causing said focused radiation to operate on select tissue within the body.

5. A medical scanning system in accordance with claim 1 wherein said transducers include means for generating operating beamed radiation at an intensity sufficient to destroy select tissue intersected thereby, and control means for said latter radiation generating means controlled by said electronic computing means to permit said beamed radiation generating means to generate and direct tissue destroying radiation at a select portion of the body of a living being supported by said second support.

6. A medical radiation scanning system in accordance with claim 1 including means for varying the intensity of radiation generated by said first transducing means and control means for said radiation intensity varying means controlled by signals generated by said electronic computing means.

7. A medical radiation scanning system in accordance with claim 1 wherein said information signals generated on the output of said second transducing means are analog image information signals and said electronic computing means includes means for digitizing said analog signals and generating trains of digital information signals, and computing means for electronically analyzing said digital information signals.

8. A medical radiation scanning system in accordance with claim 1 including a third support supported by said first support and supporting said plurality of transducers, means for moving said third support in guided movement with respect to said first support and further comprising a controllable motor means for driving said third support with respect to said first support to effect scanning movement of said transducers with respect to the body of a living being supported by said second support, wherein said controllable motor means is controlled by said electronic computing means.

9. A method for performing a medical procedure in a patient, comprising the steps of:

predeterminately locating and retaining a patient on a first support;

generating penetrating radiation from a radiation source mounted on a second support;

effecting physical changes in select tissue of said patient with a means for performing a therapeutic procedure;

detecting radiation emanating from a select portion of the patient's body which results from said penetrating radiation, said detected radiation being modulated by the physical characteristics of said select body portion including physical changes effected by said procedure performing means;

generating electrical signals in accordance with said detected radiation;

computer processing and analyzing said electrical signals to extract information therefrom, and;

employing results of said computer processing to effect controlled relative movement of said first support with respect to said second support; and employing results of said computer processing to control operation of said procedure performing means in accordance with physical changes effected therewith.

10. The method as set forth in claim 9 wherein the results of said computer processing are also employed to control the operation of said radiation source.

11. The method as set forth in claim 9 wherein said therapeutic procedure performing means performs a surgical procedure.

12. The method as set forth in claim 9 wherein said therapeutic procedure performing means generates and directs radiation at a select portion of the patient's body.

13. The method as set forth in claim 9 wherein the radiation emanating from a select portion of the patient's body is detected during controlled relative movement of said first support with respect to said second support.

* * * * *